United States Patent [19]

Seres et al.

[11] 4,364,958

[45] Dec. 21, 1982

[54] 1-SUBSTITUTED-3-CYCLOALKYL-SULFO-NYL-PYRROLIDINE-2,5-DIONE DERIVATIVES AND FUNGICIDAL COMPOSITIONS THEREOF

[75] Inventors: Jenö Seres, Erika Varkonyi, née Schlavicskó, Sándor Virag, Gábor Kulcsár, all of Budapest, Hungary

[73] Assignee: Chinoin Gyogyszer es Vegyeszeti Termekek Gyara Rt., Budapest, Hungary

[21] Appl. No.: 169,439

[22] Filed: Jul. 16, 1980

[30] Foreign Application Priority Data

Jul. 17, 1979 [HU] Hungary .............................. CI 1951

[51] Int. Cl.³ .................. C07D 207/416; A01N 43/36
[52] U.S. Cl. ..................................... 424/274; 548/544
[58] Field of Search .................. 260/326.41, 326.5 SF

[56] References Cited

U.S. PATENT DOCUMENTS

3,538,114 11/1970 Himmele et al. ............... 260/326.41
3,804,856 4/1974 Ooba et al. .................. 260/326.5 SF

FOREIGN PATENT DOCUMENTS

752109 12/1970 Belgium ..................... 260/326.5 SF
2143601 3/1972 Fed. Rep. of Germany .
70/01621 3/1970 South Africa .

OTHER PUBLICATIONS

Kato, Bull. Chem. Soc., Japan, 48, 3675–3677, (1975).
Hackh's Chemical Dictionary.

*Primary Examiner*—Mark L. Berch
*Attorney, Agent, or Firm*—Karl F. Ross

[57] ABSTRACT

A fungicidal compound of the formula:

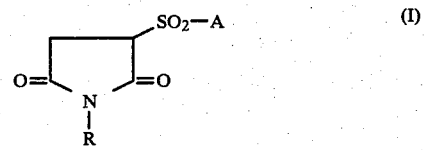

wherein A is $C_{5-10}$ cycloalkyl, R is hydrogen, $C_{1-6}$ alkyl, phenyl optionally substituted by one or more groups selected from $C_{1-4}$ alkyl, nitro, hydroxy, carboxy, sulfo, sulfonylamino, halogen, $C_{1-4}$ alkoxy, $C_{1-4}$ acyloxy, $C_{2-5}$ alkoxycarbonyl, $C_{1-4}$ acyl, and N-($C_{2-5}$ alkoxycarbonyl)-sulfonylamino, or phenyl-($C_{1-4}$ alkyl) or a salt thereof.

23 Claims, No Drawings

1-SUBSTITUTED-3-CYCLOALKYL-SULFONYL-PYRROLIDINE-2,5-DIONE DERIVATIVES AND FUNGICIDAL COMPOSITIONS THEREOF

The invention relates to new 1-substituted-3-cycloalkyl-sulfonyl-pyrrolidine-2,5-dione derivatives of the formula I as well as to fungicidal compositions containing the new compounds as active ingredients and a process for the preparation of the compositions.

In the formula I

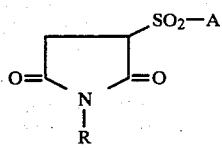　　　(I)

A is $C_{5-10}$ cycloalkyl,
R is hydrogen, $C_{1-6}$ alkyl, phenyl optionally substituted by one or more of $C_{1-4}$ alkyl, nitro, hydroxy, carboxy, sulfo, halogen, $C_{1-4}$ alkoxy, $C_{1-4}$ acyloxy, $C_{2-5}$ alkoxycarbonyl, or $C_{1-4}$ acyl, or phenyl-($C_{1-4}$ alkyl).

The new 1-substituted 3-cycloalkyl-sulfonyl-pyrrolidine-2,5-dione derivatives possess strong fungicidal activity and thus are suitable for combatting human, veterinary and phytopathological fungi.

N-(3,5-dihalophenyl)-3(,4)-(di)-substituted-pyrrolidine-2,5-dione derivatives have been reported to possess antimicrobial activity (South African Patent Specification No. 701 624).

Compounds of similar structure, i.e. N-(2,6-disubstituted-phenyl)-3-substituted-pyrrolidine-2,5-dione derivatives are disclosed in West-German Patent Publication No. 2 143 601. The compounds display antimicrobial activity.

The coupling reaction of N-aryl-maleinimides and phenyl sulfinic acid is disclosed in Bull. of the Chem. Soc. of Japan 48 (12), 3675-3677 (1975). No utility of the compounds is disclosed in the article.

As microbes become resistant to the active ingredients used, therapy continuously requires new antimicrobial ingredients.

It has been found that the new 1-substituted-3-cycloalkyl-sulfonyl-pyrrolidine-2,5-dione derivatives of the formula I possess antimicrobial, mainly fungicidal activity, even against microorganisms which have become resistant to the conventionally used fungicidally active ingredients.

According to the invention the new 1-substituted-3-cycloalkyl-sulfonyl-pyrrolidine-2,5-dione derivatives are prepared by (a₁) coupling a cycloalkyl-thiol of the formula III

HS—A　　(III)

with a 1-substituted-pyrroline-2,5-dione of the formula II

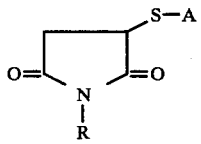　　(II)

and oxidizing the obtained 1-substituted-3-cycloalkylthio-pyrrolidine-2,5-dione derivative of the formula IV

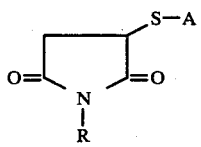　　(IV)

or (a₂) oxidizing a 1-substituted-3-cycloalkylthio-pyrrolidine-2,5-dione of the formula IV

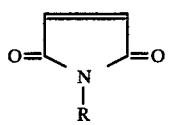　　(IV)

(b) coupling a cycloalkyl-sulfinic acid of the formula V

HO—SO—A　　(V)

with a 1-substituted-pyrroline-2,5-dione of the formula II

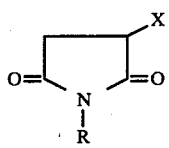　　(II)

or (c) reacting a 1-substituted-3-halo-pyrrolidine-2,5-dione of the formula VI

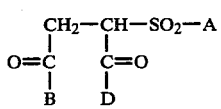　　(VI)

with an alkali metal sulfonate of the formula VI

Me—O—SO—A　　(VII)

or (d) treating a cycloalkyl-sulfonyl-succinic acid semi-amide of the formula VIII

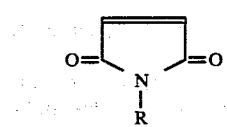　　(VIII)

where X is halogen, with an alkali metal sulfinate of the formula VII —NH—R— wherein R is as given above—with a water binding agent.

The reaction of 1-substituted-pyrroline-2,5-dione of the formula II and cycloalkyl-thiol of the formula III according to process variant (a₁) may optionally be carried out in the presence of an inert organic solvent and/or a basic catalyst. As suitable organic solvents aromatic hydrocarbons, such as benzene, ethers, such as dioxane, alcohols, such as ethanol may be employed. As basic catalysts organic or inorganic basis are preferred. As examples for the basic catalysts triethylamine or triethylene diamine may be mentioned. Reactants of the formula II and III are preferably used in equimolar amounts, but in some cases one of the reactants may be employed in excess. 1-substituted-3-cycloalkylthio-pyrrolidine-2,5-dione derivatives of the formula IV obtained in the course of the above reaction may be recovered by evaporation of the reaction mixture. The evaporation may be performed at atmospheric pressure or at reduced pressure.

1-Substituted-3-cycloalkylthio-pyrrolidine-2,5-dione derivatives of the formula IV may be oxidized by dissolving or suspending the compound in an inert solvent, such as water, lower ketones, such as acetone, lower alkane carboxylic acids, lower alkane carboxylic acid anhydrides, or a suitable mixture of the mentioned solvents, such as an 1:1 mixture of acetic acid and acetic anhydride and oxidizing the obtained product preferably at 0° to 50° C. with an oxidizing agent, such as hydrogen peroxide or potassium permanganate. The oxidizing agent is preferably used in excess.

Compounds of the formulae II and V according to process variant (b) are reacted preferably by dissolving or suspending the compound of the formula II in a mixture of water and a lower alkanol and cycloalkyl sulfinic acid of the formula V is added to this solution or suspension under stirring preferably at 0° to 25° C. Under the above-mentioned conditions the reaction is completed within a few hours and—the compound of the formula I is precipitating from the reaction mixture.

1-substituted-3-halo-pyrrolidine-2,5-dione of the formula VI and alkali metal-sulfinate of the formula VII are preferably reacted in an inert polar aprotic solvent, such as dimethylformamide. When using equimolar reactants, the reaction is complete within 30–120 minutes at a temperature ranging from 15° to 35° C.

Dehydration of cycloalkyl-sulfonyl-succinic acid semiamides of the formula VIII is preferably conducted in an excess of the water binding agent, such as phosphorus pentoxide, phosphorus trichloride, acetyl chloride, acetic anhydride. Dehydration is preferably performed in an inert organic solvent. It is particularly preferred to use the same substance as water binding agent and as solvent. Acetic anhydride may be used for example as a solvent and as a water binding agent as well. The reaction may be accelerated by heating. The reaction temperature is generally within a range from 20° C. to 140° C., preferably from 90° to 95° C.

The formed compounds of the formula I are precipitated from the mixture or are isolated by filtration, centrifuging or remain in the solution. In the latter case the reaction mixture is usually processed by isolating the by-products—if any—by filtration followed by pouring the reaction mixture on ice or water and isolating the thus precipitated product. According to another method the volatile components and the solvent are distilled off from the mixture optionally at reduced pressure and the obtained residue is purified by recrystallization. Recovery and purification of the end products may be conducted by any other conventionally used technique.

The lower alkyl, alkoxy, alkanoyl and alkane carboxylic acid and alkane carboxylic acid anhydride groups of the invention contain alkyl groups having 1 to 4 carbon atoms.

Compounds of the formulae II, V, VII, VI and VIII used as starting materials in the process according to the invention are known or may be obtained by methods known per se. 1-Substituted 3-pyrroline-2,5-diones of the formula II may be obtained by reacting maleic acid anhydride with a corresponding amine followed by treating the obtained 4-substituted-amino-4-oxobutenoic acid with a water binding agent. (Wiss. Z. Univ. Halle XXV' 76M, 4, 5 (1976) and J. Org. Chem., 26, 2037 (1961).

Sulfinic acids of the formula V and salts thereof of the formula VII may be prepared by methods disclosed in the state of art (J. Amer. Chem. Soc., 61, 3089 (1939), Org. Synth., Coll. Vol. I 492 (1943), J. Org. Chem., 17, 1529 (1952) and the cited references.

1-Substituted 3-halo-pyrrolidine-2,5-diones of the formula VI may be prepared by similar methods as disclosed in Obscs. Him., 26, 208 (1956), J. Org. Chem. 28, 1713 (1963) and South African Pat. Spec. No. 70.01624.

Compounds of the formula VIII may be prepared for example by coupling 4-substituted amino-4-oxobutenoic acids with cycloalkyl-thiols-prepared as given above—according to process variant ($a_1$) and oxidizing the obtained product as disclosed in process variant ($a_2$).

Some of the starting materials are commercially available. The fungicidal activity of the compounds of the formula I of the invention was investigated as follows:

Sabouraud medium was inoculated with $10^5$/ml. germ number and the propagation of the fungi was examined after 24, 48, 72, 144 and 288 hours incubation time and the minimal inhibitory concentrations were determined.

The obtained results are summarized in Tables I and II.

The following test organisms were used.

| | |
|---|---|
| Saccharomyces cerevisiae OKI.1282 | "1" |
| Candida albicans CBS.562 | "2" |
| Candida tropicalis CBS.433 | "3" |
| Aspergillus niger CBS.12648 | "4" |
| Aspergillus niger CCM.F-330 | "20" |
| Aspergillus fumigatus CBS.11326 | "5" |
| Aspergillus flavus CBS.24765 | "6" |
| Penicillium digitatum CBS.31948 | "7" |
| Penicillium digitatum CCM.F-382 | "8" |
| Penicillium chrysogenium CBS.19646 | "9" |
| Penicillium chrysogenium CCM.F-362 | "10" |
| Microsporum gypseum ver. vinosum CBS.10064 | "11" |
| Sporotrichum schenkii CBS.34035 | "12" |
| Trichophyton rubrum CBS.30338 | "13" |
| Trichophyton mentagrophytes CBS.50148 | "14" |
| Epidermophyton floccosum OKI/IV. | "15" |
| Fusarium graminocorum DSM.11802 | "16" |
| Fusarium oxysporum DSM.10975 | "17" |
| Fusarium monoliforme DSM.11778 | "18" |
| Fusarium culmorum DSM.11425 | "19" |
| Candida krusei 79/K47 | "21" |
| Cryptococcus neoform. 78/K16 | "22" |

In the Tables the names of the microorganisms are replaced by their number as given above.

Abbreviations after the name of the microorganisms:
CBS.: Centralbureau voor Schimmelcultures, Baarn, Netherlands
CCM.: Czechoslovak Collection of Microorganism, J. E. Purkyne, University Brno, C6SR.
DSM.: Deutsche Sammlung für Mikroorganismen, Institute of Mycology, Berlin-Dahlem, Federal Republic of Germany, OKI.: Országos Közegészségtani Intézet, Budapest.
LD$_{50}$ of N-pheny-3-cyclohexyl-sulfonyl-pyrrolidine-2,3-dione when applied intraperitoneally female mice: 382 mg./kg.
male mice: 461 mg./kg.
No toxic properties of the compounds were observed when administered perorally.

TABLE I

| Test-micro-organism | 1-phenyl-3-cyclohexyl-sulfonyl-pyrrolidine-2,5-dione | | | | | | 1-(p-tolyl)-3-cyclohexyl-sulfonyl-pyrrolidine-2,5-dione | | | | | |
|---|---|---|---|---|---|---|---|---|---|---|---|---|
| | minimal inhibitory concentrations μg/ml | | | | | | | | | | | |
| | 24 | 48 | 72 | 144 | 288 | hours | 24 | 48 | 72 | 144 | 288 | hours |
| "1" | 50 | 50 | — | — | — | | 25 | 25 | — | — | — | |
| "2" | 75 | 100 | — | — | — | | 25 | 50 | — | — | — | |
| "3" | 150 | 150 | — | — | — | | 100 | 150 | — | — | — | |
| "4" | — | — | 75 | 150 | 150 | | — | — | 25 | 75 | 75 | |
| "5" | — | — | 50 | 150 | 150 | | — | — | 50 | 150 | 150 | |
| "6" | — | — | 100 | 200 | 250 | | — | — | 150 | 250 | — | |
| "7" | — | — | 10 | 25 | 25 | | — | — | 10 | 10 | 10 | |
| "8" | — | — | 25 | 50 | 75 | | — | — | 25 | 25 | 75 | |
| "9" | — | — | 50 | 75 | 75 | | — | — | 50 | 75 | 75 | |
| "10" | — | — | 75 | 200 | 200 | | — | — | 75 | 150 | 150 | |
| "11" | — | — | 10 | 10 | 10 | | — | — | 10 | 25 | 25 | |
| "12" | — | — | 10 | 10 | 50 | | — | — | 5 | 10 | 25 | |
| "13" | — | — | 2.5 | 10 | 10 | | — | — | 2.5 | 5 | 5 | |
| "14" | — | — | 5 | 10 | 10 | | — | — | 2.5 | 2.5 | 5 | |
| "15" | — | — | 2.5 | 5 | 5 | | — | — | 5 | 5 | 5 | |
| "16" | — | — | 50 | 100 | 100 | | — | — | 50 | 50 | 50 | |
| "17" | — | — | 50 | 75 | 75 | | — | — | 150 | 200 | 200 | |
| "18" | — | — | 100 | 150 | 150 | | — | — | 100 | 150 | 150 | |
| "19" | — | — | 50 | 50 | 100 | | — | — | 75 | 150 | 150 | |
| "20" | — | — | 150 | 200 | 250 | | — | — | 100 | 150 | 250 | |
| "1" | 75 | 75 | — | — | — | | 10 | 25 | — | — | — | |
| "2" | 50 | 50 | — | — | — | | 10 | 25 | — | — | — | |
| "3" | 75 | 75 | — | — | — | | — | — | — | — | — | |
| "4" | — | — | 75 | 150 | 150 | | — | — | 25 | 50 | 75 | |
| "5" | — | — | 50 | 150 | 200 | | — | — | — | — | — | |
| "6" | — | — | 75 | 150 | 200 | | — | — | — | — | — | |
| "7" | — | — | 10 | 25 | 50 | | — | — | 10 | 10 | 10 | |
| "8" | — | — | 10 | 50 | 50 | | — | — | — | — | — | |
| "9" | — | — | 50 | 75 | 150 | | — | — | — | — | — | |
| "10" | — | — | 75 | 150 | 200 | | — | — | — | — | — | |
| "11" | — | — | 10 | 25 | 25 | | — | — | — | — | — | |
| "12" | — | — | 50 | 75 | 100 | | — | — | 5 | 25 | 25 | |
| "13" | — | — | 2.5 | 10 | 10 | | — | — | 1 | 2.5 | 2.5 | |
| "14" | — | — | 2.5 | 10 | 25 | | — | — | 2.5 | 2.5 | 5 | |
| "15" | — | — | 1 | 2.5 | 10 | | — | — | 2.5 | 5 | 5 | |
| "17" | — | — | 50 | 75 | 75 | | — | — | — | — | — | |
| "18" | — | — | 75 | 150 | 200 | | — | — | — | — | — | |
| "20" | — | — | 75 | 150 | 150 | | — | — | — | — | — | |
| "21" | 10 | 10 | — | — | — | | — | — | — | — | — | |
| "22" | 25 | 25 | — | — | — | | — | — | — | — | — | |

TABLE II

| Test-micro-organism | 1-(p-nitrophenyl)-3-cyclohexylsulfonyl-pyrrolidine-2,5-dione | | | | | | 3-cyclohexylsulfonyl-pyrrolidine-2,5-dione | | | | | | 1-(2-acetoxy-4-methoxycarbonyl-phenyl)-3-cyclohexylsulfonyl-pyrrolidine-2,5-dione | | | | | |
|---|---|---|---|---|---|---|---|---|---|---|---|---|---|---|---|---|---|---|
| | minimal inhibitory concentrations μg/ml | | | | | | | | | | | | | | | | | |
| | 24 | 48 | 72 | 144 | 288 | hours | 24 | 48 | 72 | 144 | 288 | hours | 24 | 48 | 72 | 144 | 288 | hours |
| "1" | 25 | 50 | — | — | — | | — | — | — | — | — | | — | — | — | — | — | |
| "2" | 75 | 150 | — | — | — | | — | — | — | — | — | | — | — | — | — | — | |
| "4" | — | — | 75 | 150 | 150 | | — | — | — | — | — | | — | — | 200 | 200 | 200 | |
| "7" | — | — | 100 | 150 | 150 | | — | — | 50 | 50 | 50 | | — | — | 50 | 50 | 100 | |
| "12" | — | — | 25 | 25 | 25 | | — | — | 150 | 150 | 150 | | — | — | 50 | 100 | 150 | |
| "13" | — | — | 75 | 75 | 150 | | — | — | 50 | 75 | 75 | | — | — | 25 | 25 | 50 | |
| "14" | — | — | 75 | 100 | 100 | | — | — | 50 | 50 | 75 | | — | — | 2.5 | 2.5 | 2.5 | |
| "15" | — | — | 100 | 150 | 150 | | — | — | 25 | 25 | 25 | | — | — | 10 | 10 | 10 | |

| Test micro-organism | 1-(o-tolyl)-3-cyclohexyl-sulfonyl-pyrrolidine-2,5-dione | | | | | | 1-m(tolyl)-3-cyclohexyl-sulfonyl-pyrrolidine-2,5-dione | | | | | | 1-(p-methoxyphenyl)-3-cyclohexylsulfonyl-pyrrolidine-2,5-dione | | | | | |
|---|---|---|---|---|---|---|---|---|---|---|---|---|---|---|---|---|---|---|
| | minimal inhibitory concentrations μg/ml | | | | | | | | | | | | | | | | | |
| | 24 | 48 | 72 | 144 | 288 | hours | 24 | 48 | 72 | 144 | 288 | hours | 24 | 48 | 72 | 144 | 288 | hours |
| "1" | 25 | 25 | — | — | — | | 25 | 25 | — | — | — | | 25 | 50 | — | — | — | |
| "2" | 75 | 100 | — | — | — | | 50 | 100 | — | — | — | | 50 | 150 | — | — | — | |
| "4" | — | — | 100 | 150 | 150 | | — | — | 75 | 100 | 150 | | — | — | 75 | 100 | 150 | |
| "7" | — | — | 10 | 50 | 50 | | — | — | 10 | 25 | 25 | | — | — | 100 | 100 | 150 | |
| "12" | — | — | 10 | 25 | 50 | | — | — | 10 | 25 | 50 | | — | — | 5 | 10 | 10 | |
| "13" | — | — | 10 | 25 | 50 | | — | — | 5 | 10 | 25 | | — | — | 10 | 10 | 10 | |
| "14" | — | — | 10 | 25 | 25 | | — | — | 5 | 25 | 50 | | — | — | 2.5 | 75 | 100 | |

TABLE II-continued

| Test-microorganism | 1-(p-acetylphenyl)-3-cyclohexylsulfonyl-pyrrolidine-2,5-dione | | | | | | 1-(o-chlorphenyl)-3-cyclohexylsulfonyl-pyrrolidine-2,5-dione | | | | | | 1-(m-chlorphenyl)-3-cyclohexylsulfonyl-pyrrolidine-2,5-dione | | | | | |
|---|---|---|---|---|---|---|---|---|---|---|---|---|---|---|---|---|---|---|
| | minimal inhibitory concentrations μg/ml | | | | | | | | | | | | | | | | | |
| | 24 | 48 | 72 | 144 | 288 | hours | 24 | 48 | 72 | 144 | 288 | hours | 24 | 48 | 72 | 144 | 288 | hours |
| "15" | — | — | 5 | 10 | 10 | | — | — | 5 | 10 | 25 | | — | — | 5 | 25 | 75 | |
| "1" | 25 | 50 | — | — | — | | 25 | 75 | — | — | — | | 10 | 25 | — | — | — | |
| "2" | 50 | 75 | — | — | — | | 50 | 50 | — | — | — | | 25 | 75 | — | — | — | |
| "4" | — | — | 75 | 150 | 150 | | — | — | 50 | 150 | 150 | | — | — | 50 | 100 | 100 | |
| "7" | — | — | 75 | 100 | 150 | | — | — | 25 | 50 | 50 | | — | — | 10 | 50 | 50 | |
| "12" | — | — | 5 | 25 | 25 | | — | — | 10 | 50 | 50 | | — | — | 10 | 25 | 25 | |
| "13" | — | — | 10 | 25 | 50 | | — | — | 2.5 | 10 | 10 | | — | — | 2.5 | 2.5 | 2.5 | |
| "14" | — | — | 10 | 25 | 25 | | — | — | 2.5 | 5 | 5 | | — | — | 2.5 | 2.5 | 2.5 | |
| "15" | — | — | 25 | 50 | 75 | | — | — | 2.5 | 5 | 10 | | — | — | 2.5 | 5 | 10 | |

| Test-microorganism | 1-(o-nitrophenyl)-3-cyclohexyl-sulfonyl-pyrrolidine-2,5-dione | | | | | | 1-(m-nitrophenyl)-3-cyclohexyl-sulfonyl-pyrrolidine-2,5-dione | | | | | |
|---|---|---|---|---|---|---|---|---|---|---|---|---|
| | minimal inhibitory concentrations μg/ml. | | | | | | | | | | | |
| | 24 | 48 | 72 | 144 | 288 | hours | 24 | 48 | 72 | 144 | 288 | hours |
| "1" | 100 | 200 | — | — | — | | 75 | 75 | — | — | — | |
| "2" | 75 | 150 | — | — | — | | 50 | 100 | — | — | — | |
| "4" | — | — | 150 | 200 | 200 | | — | — | 75 | 150 | 150 | |
| "7" | — | — | 25 | 50 | 50 | | — | — | 25 | 50 | 50 | |
| "12" | — | — | 10 | 50 | 50 | | — | — | 25 | 75 | 75 | |
| "13" | — | — | 50 | 50 | 75 | | — | — | 5 | 5 | 5 | |
| "14" | — | — | 75 | 150 | 150 | | — | — | 2.5 | 5 | 25 | |
| "15" | — | — | 75 | 100 | 150 | | — | — | 5 | 10 | 10 | |

Minimal inhibitory concentrations in μg/ml medium of 1-(p-tolyl)-3-cyclohexyl-sulfonyl-pyrrolidine-2,5-dione are given after 24 and 48 hours observation period for the most important pathogenic proliferating fungi:

| proliferating fungi | minimal inhibitory concentration | |
|---|---|---|
| | 24 hours | 48 hours |
| Candida benhamii | 25 | 75 |
| Candida guilliermondii | 5 | 10 |
| Candida humicola | 5 | 25 |
| Candida krusei (79/K47) | 2.5 | 10 |
| Candida lipolytic | 5 | 10 |
| Candida parapsilosis | 10 | 50 |
| Candida pseudotropic | 2.5 | 10 |
| Candida valida | 5 | 10 |
| Candida vini | 1 | 5 |
| Cryptococcus neoform (78/K16) | 1 | 10 |

The given minimal inhibitory concentrations completely inhibited the growth of the microorganisms. As a medium Saboroud medium was employed.

1-(p-Tolyl)-3-cyclohexyl-sulfonyl-pyrrolidine-2,5-dione and 1-phenyl-3-cyclohexyl-sulfonyl-pyrrolidine-2,5-dione were active against the following phytopathogenic fungi too: Botrytis cinerea, Ascochyta pisi, Cercospora beticola, Taphrina deformans, Phytophtora infestans, Sclerotinia sclerotiorum, Verticillium albo-atrum, Verticillium dahlise and Venturia.

The 1-substituted-3-cycloalkyl-sulfonylpyrrolidine-2,5-dione derivatives of the invention may be used due to their strong fungicidal activity as active ingredients of fungicidal compositions. One or more compounds of the formula I may be formulated by using the conventional filling agents, diluents, stabilizing and/or flavoring agents and/or formulating excipients. The compositions may be in solid, liquid or semi-liquid form. As solid compositions tablets, capsules, troches, pellets, pills and powders may be mentioned. The tablets may be scored. The coating of the dragees and the capsules may optionally be indicated by a color code according to the active ingredient content. As liquid preparations lotions, sprayable formulations, dressing agents, liquid medicines, injectable solutions, aerosols etc. may be used. As semi-liquid compositions ointments, pastes or creams may be used.

Fungicidal compositions according to the invention contain as main active ingredient a compound of the formula I or a salt thereof in an amount of 1–80%—wherein R and A are as given above—and 0–20% colloidal silicic acid, 0–10% surfactant, 0–20% mineral filling agent, 0–5% mucous substance, 0–10% protective colloid, 0–80% starch, 0–50% glycerol, 0–15% water, 0–99% indifferent, atoxic organic solvent and 0–60% spray propellant.

The following Examples show details of the preparation of the compounds of the formula I and of the fungicidal compositions containing a compound of the formula I as active ingredient. The Examples serve for illustration and not for limitation.

EXAMPLE 1

3-Cyclohexyl-sulfonyl-pyrrolidine-2,5-dione

In a mixture of 15 ml. of glacial acetic acid and 15 ml. of acetic anhydride 3.19 g. (0.015 mole) of 3-cyclohexylthio-pyrrolidine-2,5-dione are suspended. 7.2 ml. (0.075 mole) of a 30% hydrogen peroxide solution is added dropwise to the suspension under stirring and cooling with icy water and the system is then completely dissolved at room temperature. The solution is then cooled down again to a temperature ranging from 0° C. to 5° C. and stirred for 5 hours at this temperature. The mixture is then allowed to stand overnight and poured to crushed ice. The precipitated product is filtered off and washed with water to remove acid. 2.6 g. (71%) of the named product are obtained. M.p.: 159°–160° C. After recrystallization from water m.p.: 160°–162° C. Minimal inhibitory concentration: inhibiting the growth of Trychophyton metagrophytes: 50 μg./ml. of Epidermophyton floccosum: 25 μg./ml.

EXAMPLE 2

1-Phenyl-3-cyclohexyl-sulfonyl-pyrrolidine-2,5-dione

In a mixture of 10 ml. of glacial acetic acid and 10 ml. of acetic acid anhydride 2.89 g. (0.01 mole) of 1-phenyl-3-cyclohexylthio-pyrrolidine-2,5-dione are suspended. A 30% solution of 4.8 ml. (0.5 mole) hydrogen peroxide is added dropwise to the suspension under cooling with icy water and stirring. The reaction mixture is maintained at room temperature by external cooling until a complete solution is obtained whereafter the mixture is stirred for 5 hours under cooling with ice and water. The mixture is allowed to stand for one day and the precipitated product is filtered and washed with water to remove acid. 3.18 g. of the named compound are obtained. Yield: 99%. M.p.: 149°–151° C.

EXAMPLE 3

1-Phenyl-3-cyclohexyl-sulfonyl-pyrrolidine-2,5-dione

A solution of 0.296 g. (0.002 mole) of cyclohexyl sulfinic acid in 100 ml. of water is added to a solution of 0.346 g. (0.002 mole) 1-phenyl-pyrroline-2,5-dione in 100 ml. of ethanol at 15° C. under stirring. When the addition is completed the reaction is stirred for further 10 hours at 15° C. The precipitated product is filtered and washed with water. 0.475 g. (74%) of the named product is obtained, m.p.: 149°–151° C.

EXAMPLE 4

1-Phenyl-3-cyclohexyl-sulfonyl-pyrrolidine-2,5-dione

To a solution of 2.54 g. (0.01 mole) of 1-phenyl-3-bromo-pyrrolidine-2,5-dione in 50 ml. of dimethylformamide 1.70 g. (0.01 mole) of sodium cyclohexyl-sulfinate are added at 30° C. under stirring. The stirring is then continued for 2 hours and the reaction mixture is then diluted with water to a tenfold volume and the precipitated named compound is filtered. After washing and drying 2.63 g. (82%) of the named compound are obtained, m.p.: 148°–151° C.

EXAMPLE 5

1-Phenyl-3-cyclohexyl-sulfonyl-pyrrolidine-2,5-dione 3.39 g. (0.01 mole) of 2-cyclohexyl-sulfonyl-4-phenylamino-4-oxo-butanoic acid are dissolved in 20 ml. of acetic acid anhydride and 0.82 g. (0.01 mole) anhydrous sodium acetate and the solution is heated for 1 hour at 100° C. The reaction mixture is then poured on crushed ice and the precipitated compound named filtered off and washed with water in order to remove acid. 2.76 g. (86%) of the named compound are obtained. M.p.: 149°–151° C. After recrystallization from methanol m.p.: 150°–152° C. Minimal inhibitory concentration inhibiting the growth of *Trychophyton mentagrophytes:* 2.5 μg/ml. and of *Epidermophyton floccosum:* 1.0 μg./ml.

EXAMPLE 6

1-(p-Tolyl)-3-cyclohexyl-sulfonyl-pyrrolidine-2,5-dione 4.54 g. (0.015 mole) 1-(p-tolyl)-3-cyclohexylthiopyrrolidine-2,5-dione are suspended in a mixture of 15 ml. of glacial acetic acid and 15 ml. of acetic acid anhydride and under cooling with icy water and under stirring 7.2 ml. (0.075 mole) of 30% hydrogen peroxide solution is added dropwise. The reaction mixture is kept at room temperature until a complete solution is obtained. The mixture is then cooled to 0° to 5° C. and the mixture is stirred at this temperature for 5 hours. The reaction mixture is allowed to stand overnight whereafter the precipitating mixture is filtered and washed with water in order to remove acid. 4.84 g. (97%) of the named compound are obtained. M.p.: 166°–168° C. After recrystallization from methanol the product melts at 170°–171° C.

Minimal inhibitory concentration inhibiting the growth of *Trichophyton mentagrophytes:* 2.5 μg./ml., of *Epidermophyton floccosum:* 5.0 g./ml.

EXAMPLE 7

1-(3-Acetoxy-4-methoxycarbonyl-phenyl)-3-cyclohexyl-sulfonyl-pyrrolidine-2,5-dione 4.05 g. (0.01 mole) of 1-(3-acetoxy-4-methoxycarbonyl-phenyl)-3-cyclohexylthio-pyrrolidine-2,5-dione are suspended in a mixture of 10 ml. of glacial acetic acid and 10 ml. of acetic acid anhydride. A 30% solution of 4.8 ml. (0.05 mol) hydrogen peroxide is added dropwise. The reaction mixture is stirred at room temperature until it is completely dissolved and the mixture is then stirred for further 5 hours under cooling with ice and water. The pure solution is allowed to stand overnight, poured on ice, the precipitated product is filtered and acid is removed by washing with water. 3.8 g. (87%) of the named compound is obtained. M.p.: 174°–176° C. After recrystallization from methanol the product melts at 177°–178° C.

Minimal inhibitory concentration: inhibiting the growth of *Trichophyton metagrophytes:* 2.5 μg./ml. and of *Epidermophyton floccosum* is 10 μg./ml.

EXAMPLE 8

1-(3-Acetoxy-4-carboxy-phenyl)-3-cyclohexyl-sulfonyl-pyrrolidine-2,5-dione 8.24 g. (0.03 mole) of 1-(3-acetoxy-4-carboxyphenyl)-pyrroline-2,5-dione are dissolved in 80 ml. of dioxane and 3.6 ml. (0.03 mole) of cyclohexane-thiol are added. Two drops of triethylamine catalyst are then added dropwise to the reaction mixture and the mixture is kept at 80°–90° C. for 4 hours. The solvent is distilled off in vacuo. As a residue an oily 1-(3-acetoxy-4-carboxyphenyl)-3-cyclohexylthio-pyrrolidine-2,5-dione is obtained. The product is dissolved in a mixture of 30 ml. of glacial acetic acid and 30 ml. of acetic anhydride and under cooling with icy water and stirring 14.4 ml. (0.15 mole) of a 30% hydrogen peroxide solution are added dropwise. The cooling is ceased and the reaction mixture is allowed to warm up to 30° C. The mixture is the cooled again with icy water to 0° to 5° C. and stirred at this temperature for 5 hours. The reaction mixture is allowed to stand overnight. The next day the pure solution is poured on ice and the precipitated product is filtered and washed with water to remove acid. M.p.: 155°–158° C. Yield: 6.7 g. (52.9%). After recrystallization from 50% ethanol the product melts at 160°–161° C.

According to the method disclosed in the Examples the following compounds of the formula I are prepared:
1-ethyl-3-cyclohexyl-sulfonyl-pyrrolidine-2,5-dione, yield: 47.6%, m.p.: 118°–120° C.,
1-n-hexyl-3-cyclohexyl-sulfonyl-pyrrolidine-2,5-dione, yield: 39.8%, m.p.: 127°–130° C.,
1-(2-chlorophenyl)-3-cyclohexyl-sulfonyl-pyrrolidine-2,5-dione, yield: 71.4%, m.p.: 153°–155° C.,
1-(3-nitrophenyl)-3-cyclohexyl-sulfonyl-pyrrolidine-2,5-dione, yield: 92%, m.p.: 145°–148° C.

1-(4-acetylphenyl)-3-cyclohexyl-sulfonyl-pyrrolidine-2,5-dione, yield: 79.1%, m.p.: 203°–206° C.,
1-(4-Methoxyphenyl)-3-cyclohexyl-sulfonyl-pyrrolidine-2,5-dione, yield: 85.7%, m.p.: 139°–140° C.,
1-benzyl-3-cyclohexyl-sulfonyl-pyrrolidine-2,5-dione, yield: 84%, m.p. 160°–62° C.,
1-phenyl-3-cyclopentyl-sulfonyl-pyrrolidine-2,5-dione, yield: 60.2%, m.P. 158°–159° C. (crystallized from ethanol),
1-(p-tolyl)-3-cyclopentyl-sulfonyl-pyrrolidine-2,5-dione, yield: 86.1%, m.p.: 178°–180° C. (crystallized from ethanol).
1-(p-sulfophenyl)-3-cyclohexyl-sulfonyl-pyrrolidine-2,5-dione, yield: 56.2%, m.p.: 230°–236° C.,
1-(4-methyl-2-sulfophenyl)-3-cyclohexyl-sulfonyl-pyrrolidine-2,5-dione, yield: 53.1%, m.p.: 244°–247° C.,
1-(3,4-dihydroxy-phenyl)-3-cyclohexyl-sulfonyl-pyrrolidine-2,5-dione, yield: 91.8%, m.p.: 186°–188° C.,
1-(4-methyl-3-carboxyphenyl)-3-cyclohexyl-sulfonyl-pyrrolidine-2,5-dione, yield: 46.7%, m.p.: 184°–188° C.,
1-(4-methyl-2-hydroxymethyl-phenyl)-3-cyclohexyl-sulfonyl-pyrrolidine-2,5-dione, yield: 86.2%, m.p.: 174°–177° C., and
1-phenyl-3-cyclocctyl-sulfonyl-pyrrolidine-2,5-dione.

The following Examples show the formulation of the active ingredients of the formula I into fungicidal compositions without limiting the scope of invention to the Examples.

Example a

Ointment

A homogeneous mixture is prepared in a stirring machine from the following components:

| | |
|---|---|
| active ingredient of the formula I | 2.0 g. |
| propyl-(p-hydroxy-benzoate) | 0.06 g. |
| methyl-(p-hydroxy-benzoate) | 0.14 g. |
| crystalline magnesium sulphate | 0.30 g. |
| white wax (Cera alba) | 1.00 g. glyc |
| glycerol | 5.00 g. |
| Miglyol 812* | 8.00 g. |
| liquid paraffin | 8.00 g. |
| Dehymuls F* | 8.00 g. |
| Cetiol V* | 10.00 g. |
| white vaseline | 10.00 g. |
| distilled water | up to 100.00 g. |

The obtained ointment is filled into tubes or jars.
Substances labelled with * have the following chemical components:
Miglyol 812 a mixture of esters of $C_{8-12}$ fatty acids with glycerol. It is an additive promoting the homogenization of the components. Manufacturer: Chemische Werke Witten GmbH, Witten, West Germany.
Catiol V: deciloleate: Manufacturer: Dehydag, Düsseldorf, West Germany.
Dehymuls F: an aliphatic ester mixture, emulgeator. Manufacturer: Dehydag, Düsseldorf, West Germany.

Example b

Talc

A homogeneous powder mixture is prepared from the fine powder of the following components:

| | |
|---|---|
| active ingredient of the formula I | 2.00 g. |
| colloidal silicon dioxide | 1.00 g. |
| magnesium stearate | 1.00 g. |

-continued

| | |
|---|---|
| zinc oxide | 2.00 g. |
| white clay | 5.00 g. |
| magnesium carbonate | 10.00 g. |
| talc | 79.00 g. |

The powder mixture is filled into boxes.

Example c

Aerosol composition

A mixture is obtained from the following components:

| | |
|---|---|
| active ingredient of the general formula I | 0.80 g. |
| abs. alcohol | 11.00 g. |
| Miglyol B12 | 12.00 g. |
| methylene chloride | 17.60 g. | and the mixture is filled into aerosol bottles. The bottle is supplied with a feeder valve and finally it is filled up with an aerosol propellant, such as a mixture of halogenated hydrocarbons.

The compositions (a)–(c) were subjected to the same microorganism inhibitory test as described in connection with the active ingredients. Results of the test carried out with 1-(p-tolyl)-3-cyclohexyl-sulfonyl-pyrrolidine-2,5-dione are given below.

| Test-micro-organism | ointment 24/48/72/144 hours | aerosol minimal inhibitory concentrations in μg./ml. 24/48/72/144 hours | talc 24/48/72/144 hours |
|---|---|---|---|
| "1" | 25/25/—/— | 2.5/5/—/— | 25/50/—/— |
| "2" | 25/75/—/— | 25/75/—/— | 50/75/—/— |
| "3" | 25/50/—/— | 25/50/—/— | 50/75/—/— |
| "4" | —/—/50/75 | —/—/25/50 | —/—/50/50 |
| "5" | —/—/50/100 | —/—/50/50 | —/—/75/100 |
| "7" | —/—/10/10 | —/—/2,5/10 | —/—/10/10 |
| "9" | —/—/10/75 | —/—/25/50 | —/—/25/50 |
| "12" | —/—/25/75 | —/—/10/25 | —/—/10/10 |
| "13" | —/—/10/50 | —/—/1/5 | —/—/5/10 |
| "14" | —/—/10/25 | —/—/1/2,5 | —/—/10/25 |
| "21" | 10/25/—/— | 2.5/10/—/— | 25/25/—/— |
| "22" | 25/50/—/— | 10/25/—/— | 25/25/—/— |
| "15" | —/—/5/10 | —/—/2.5/2.5 | —/—/10/10 |
| "11" | —/—/10/25 | —/—/10/10 | —/—/10/25 |
| "18" | —/—/100/100 | —/—/50/50 | —/—/75/100 |
| "17" | —/—/75/75 | —/—/25/25 | —/—/75/100 |

We claim:
1. A compound of the formula (I)

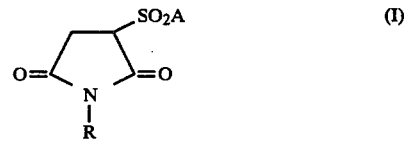

wherein
A is $C_5$ to $C_{10}$ cycloalkyl; and
R is hydrogen, $C_1$ to $C_6$ alkyl, phenyl optionally substituted by either one or two substituents wherein the substituents are selected from the group consisting of $C_1$ to $C_4$ alkyl, nitro, hydroxy, carboxy, sulfo, halogen, $C_1$ to $C_4$ alkoxy, acetoxy, $C_2$ to $C_5$ alkoxycarbonyl, and acetyl, or phenyl-($C_1$ to $C_4$ alkyl).

2. 1-Phenyl-3-cyclohexyl-sulfonyl-pyrrolidine-2,5-dione as defined in claim 1.

3. 3-Cyclohexyl-sulfonyl-pyrrolidine-2,5-dione as defined in claim 1.

4. 1-(p-Tolyl)-3-cyclohexyl-sulfonyl-pyrrolidine-2,5-dione as defined in claim 1.

5. 1-(3-Acetoxy-4-methoxycarbonyl-phenyl)-3-cyclohexyl-sulfonyl-pyrrolidine-2,5-dione as defined in claim 1.

6. 1-(3-Acetoxy-4-carboxy-phenyl)-3-cyclohexyl-sulfonyl-pyrrolidine-2,5-dione as defined in claim 1.

7. 1-Ethyl-3-cyclohexyl-sulfonyl-pyrrolidine-2,5-dione.

8. 1-n-Hexyl-3-cyclohexyl-sulfonyl-pyrrolidine-2,5-dione as defined in claim 1.

9. 1-(2-Chlorphenyl)-3-cyclohexyl-sulfonyl-pyrrolidine-2,5-dione as defined in claim 1.

10. 1-(3-Nitrophenyl)-3-cyclohexyl-sulfonyl-pyrrolidine-2,5-dione as defined in claim 1.

11. 1-(4-Acetylphenyl)-3-cyclohexyl-sulfonyl-pyrrolidine-2,5-dione as defined in claim 1.

12. A fungicidal pharmaceutical composition comprising a fungicidally effective amount of at least one 1-substituted-3-cycloalkyl-sulfonyl-pyrrolidine-2,5-dione of the formula I as defined in claim 1, together with a conventionally used fungicidally acceptable filling agent.

13. 1-(4-Methoxyphenyl)-3-cyclohexyl-sulfonyl-pyrrolidine-2,5-dione as defined in claim 1.

14. A fungicidal composition comprising about 1–80% of a compound of the formula I as defined in claim 1 fungicidally acceptable salt thereof, and 0–20% colloidal silicic acid, 0–10% surfactants, 0–20% mineral filling agents, 0–10% protective colloids, 0–80% starch, 0–50% glycerol, 0–15% water or 0–99% inert, atoxic, organic solvent and 0–60% spray propellant.

15. 1-Benzyl-3-cyclohexyl-sulfonyl-pyrrolidine-2,5-dione as defined in claim 1.

16. 1-Phenyl-3-cyclooctyl-sulfonyl-pyrrolidine-2,5-dione as defined in claim 1.

17. 1-Phenyl-3-cyclopentyl-sulfonyl-pyrrolidine-2,5-dione as defined in claim 1.

18. 1-(p-Tolyl)-3-cyclopentyl-sulfonyl-pyrrolidine-2,5-dione as defined in claim 1.

19. 1-(p-Sulfo-phenyl)-3-cyclohexyl-sulfonyl-pyrrolidine-2,5-dione as defined in claim 1.

20. 1-(4-Methyl-2-sulfo-phenyl)-3-cyclohexyl-sulfonyl-pyrrolidine-2,5-dione as defined in claim 1.

21. 1-(3,4-Dihydroxy-phenyl)-3-cyclohexyl-sulfonyl-pyrrolidine-2,5-dione as defined in claim 1.

22. 1-(4-Methyl-3-carboxy-phenyl)-3-cyclohexyl-sulfonyl-pyrrolidine-2,5-dione as defined in claim 1.

23. 1-(4-Methyl-2-hydroxymethyl-phenyl)-3-cyclohexyl-sulfonyl-pyrrolidine-2,5-dione as defined in claim 1.

* * * * *